(12) United States Patent
Miyachi et al.

(10) Patent No.: US 9,579,084 B2
(45) Date of Patent: Feb. 28, 2017

(54) ULTRASOUND DIAGNOSTIC APPARATUS

(75) Inventors: Yukiya Miyachi, Ashigara-kami-gun (JP); Masafumi Noguchi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 985 days.

(21) Appl. No.: 13/485,061

(22) Filed: May 31, 2012

(65) Prior Publication Data

US 2012/0310089 A1 Dec. 6, 2012

(30) Foreign Application Priority Data

Jun. 3, 2011 (JP) ................. 2011-125361

(51) Int. Cl.
*A61B 8/00* (2006.01)
*A61B 8/08* (2006.01)

(52) U.S. Cl.
CPC ............ *A61B 8/485* (2013.01); *A61B 8/0858* (2013.01); *A61B 8/0891* (2013.01); *A61B 8/463* (2013.01); *A61B 8/469* (2013.01); *A61B 8/5223* (2013.01); *A61B 8/486* (2013.01)

(58) Field of Classification Search
USPC ....................................................... 600/440
See application file for complete search history.

(56) References Cited

U.S. PATENT DOCUMENTS

| | | |
|---|---|---|
| 5,840,028 A | 11/1998 | Chubachi et al. |
| 6,817,982 B2 * | 11/2004 | Fritz et al. ............. 600/443 |
| 2008/0146929 A1 * | 6/2008 | Satoh ............. A61B 8/08 600/443 |
| 2010/0074475 A1 * | 3/2010 | Chouno ............. 382/107 |
| 2010/0081931 A1 * | 4/2010 | Destrempes et al. ......... 600/437 |
| 2010/0113930 A1 * | 5/2010 | Miyachi ............. 600/443 |
| 2011/0044522 A1 * | 2/2011 | Fancourt ............. G06T 7/2033 382/131 |

FOREIGN PATENT DOCUMENTS

| | | |
|---|---|---|
| JP | 06315483 A | 11/1994 |
| JP | 10-005226 A | 1/1998 |
| JP | 2004254829 A | 9/2004 |
| JP | 2010-233956 A | 10/2010 |

OTHER PUBLICATIONS

The First Office Action, dated Oct. 29, 2014, issued in corresponding CN Application No. 201210171323.8, 19 pages in English and Chinese.

* cited by examiner

*Primary Examiner* — Patricia Park
(74) *Attorney, Agent, or Firm* — Sughrue Mion, PLLC

(57) ABSTRACT

An ultrasound diagnostic apparatus comprising: an ultrasound probe which has ultrasound transducers transmitting ultrasonic waves, receiving an ultrasonic echo reflected by a subject, and outputting a reception signal according to the received ultrasonic echo; an image producer which produces a B-mode image and an M-mode image from the reception signal output from the ultrasound transducers; and a boundary detector which detects a blood vessel anterior wall boundary in the B-mode image using a time phase of the M-mode image corresponding to the B-mode image.

6 Claims, 12 Drawing Sheets

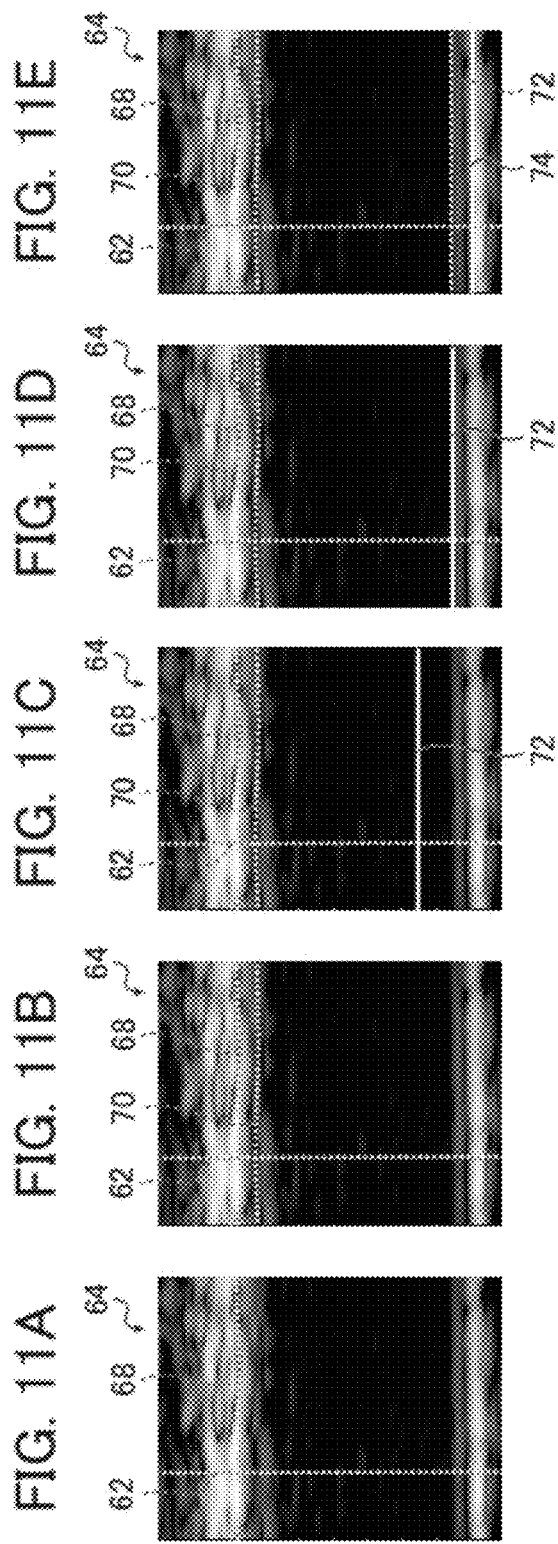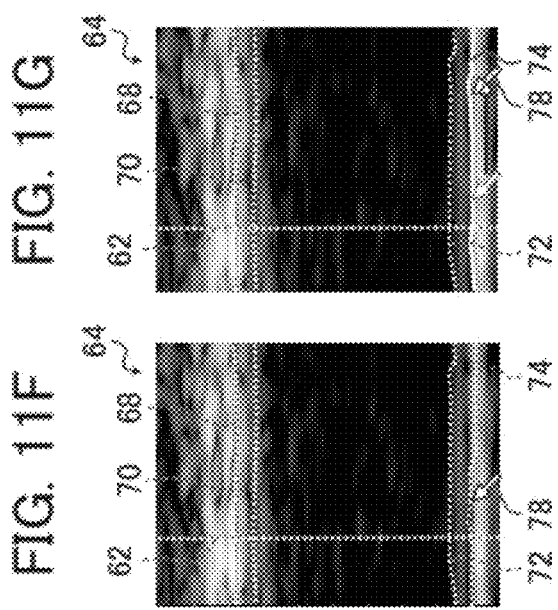

ULTRASOUND DIAGNOSTIC APPARATUS

BACKGROUND OF THE INVENTION

The present invention relates to an ultrasound diagnostic apparatus which is suitable for measuring an elastic modulus of a vascular wall, and in particular, to an ultrasound diagnostic apparatus which can automatically detect a blood vessel anterior wall boundary from a B-mode image.

An ultrasound diagnostic apparatus using an ultrasound image has hitherto been put into practical use in the field of medicine.

In general, this type of ultrasound diagnostic apparatus has an ultrasound probe (hereinafter, referred to as a probe) and a diagnostic apparatus body. Ultrasonic waves are transmitted from the probe toward a subject, an ultrasonic echo from the subject is received by the probe, and a reception signal is electrically processed by the diagnostic apparatus body to produce an ultrasound image.

Ultrasonic waves are transmitted toward a blood vessel, a cardiac wall, or the like, an ultrasonic echo therefrom is received, and a reception signal is analyzed to obtain the displacement of a vascular wall or the like. The elastic modulus of the vascular wall, the cardiac wall (heart muscle), or the like is measured from the displacement.

For example, JP 10-5226 A describes a technique in which ultrasonic waves are transmitted and received with respect to an object moving in synchronization with the heartbeats (cardiac pulsation) to obtain a reception signal of an ultrasonic echo, the instantaneous position of the object is determined using the amplitude and phase of the reception signal, and the large-amplitude displacement motion of the vascular wall based on the heartbeats is tracked, thereby obtaining the elastic modulus of the blood vessel.

Specifically, the motion velocity waveform of minute vibration of the vascular wall is obtained on the basis of the sequential position of the vascular wall, the tracking trajectory of each of the sections at a predetermined interval in the depth direction in the vascular wall is obtained, and a temporal change in thickness of each section is calculated to obtain the elastic modulus of the blood vessel.

Similarly, JP 2010-233956 A describes an ultrasound diagnostic apparatus which obtains the displacement of a blood vessel or the like from a reception signal of an ultrasonic echo obtained when ultrasonic waves are transmitted and received with respect to an object moving in synchronization with the heartbeats, and obtains an elastic modulus from the displacement.

In this ultrasound diagnostic apparatus, a B-mode image and an M-mode image are produced using a reception signal obtained from an object, such as a blood vessel. Blurring due to hand or body movement is detected from the reception signal of the M-mode image, and the positional variation of the probe and the subject is detected using the reception signal of the M-mode image where the blurring is detected. The accuracy of the reception signal is determined from the detection result, and the displacement of the object is obtained using the reception signal of the M-mode image whose accuracy is determined to be high, and the elastic modulus of the vascular wall or the like is measured from the displacement.

Such measurement of the blood vessel elastic modulus or the like in an ultrasound diagnostic apparatus is normally performed by selecting the position in the azimuth direction on the B-mode image, at which the M-mode image is displayed, using a display line (line of interest) or the like, displaying and analyzing the M-mode image of the selected display line, and detecting the shift or moving velocity of the vascular wall.

As described in JP 2010-233956 A, in the ultrasound diagnostic apparatus, the anterior wall of the blood vessel is detected with difficulty compared to the posterior wall (deep side) of the blood vessel. For this reason, in many cases, the analysis is performed using the blood vessel posterior wall.

SUMMARY OF THE INVENTION

Considering that the blood vessel has a tubular shape, in order to perform more accurate analysis, information relating to the position or displacement of the blood vessel anterior wall which is not easily detected is necessary in some cases.

In order to appropriately obtain the information relating to the position or displacement of the blood vessel anterior wall, in some cases it is necessary to appropriately recognize the position of the blood vessel anterior wall in the B-mode image, which is the tomographic image of the blood vessel, as well as in the M-mode image.

However, in the existing ultrasound diagnostic apparatus, it is very difficult to appropriately and automatically detect the blood vessel anterior wall from the B-mode image.

For this reason, when information relating to the blood vessel anterior wall in the B-mode image is necessary at the time of the measurement of the blood vessel elastic modulus or the like, for example, it is necessary for an operator, such as a physician, to observe an image and to operate a trackball or the like to set the position of the blood vessel anterior wall (blood vessel anterior wall boundary). Meanwhile, there are many cases where a boundary of the blood vessel anterior wall in the B-mode image is unclear and not easily identified visually. As a result, setting the blood vessel anterior wall in the B-mode image imposes a heavy burden on the operator.

An object of the invention is to solve the problems with the prior art, and to provide an ultrasound diagnostic apparatus which performs measurement of the blood vessel elastic modulus or the like having advantages of suitably detecting the blood vessel anterior wall boundary from the B-mode image, thereby improving operability at the time of measurement of the blood vessel elastic modulus or the like and enabling more accurate measurement.

In order to achieve the above object, the present invention provides an ultrasound diagnostic apparatus comprising: an ultrasound probe which has ultrasound transducers transmitting ultrasonic waves, receiving an ultrasonic echo reflected by a subject, and outputting a reception signal according to the received ultrasonic echo; an image producer which produces a B-mode image and an M-mode image from the reception signal output from the ultrasound transducers; and a boundary detector which detects a blood vessel anterior wall boundary in the B-mode image using a time phase of the M-mode image corresponding to the B-mode image.

In the inventive ultrasound diagnostic apparatus as above, the boundary detector preferably binarizes the M-mode image to detect a temporary lumen, detects a maximum luminance position within 3 mm in a depth direction from the temporary lumen in a time phase of the M-mode image corresponding to a B-mode image in which the blood vessel anterior wall boundary is detected, and sets the maximum luminance position as a blood vessel anterior wall boundary in the B-mode image.

Preferably, the image producer produces M-mode images corresponding to a plurality of points in the azimuth direction of the B-mode image.

Also preferably, the image producer produces M-mode images corresponding to the entire region in the azimuth direction of the B-mode image.

It is preferable that the boundary detector detects the maximum luminance position in a time phase corresponding to a B-mode image, in which the blood vessel anterior wall boundary is detected, using M-mode images corresponding to a plurality of points in the azimuth direction of the B-mode image.

It is also preferable that the boundary detector detects the maximum luminance position in a predetermined region of the M-mode image including a time phase corresponding to a B-mode image in which the blood vessel anterior wall boundary is detected.

It is also preferable that the boundary detector detects the maximum luminance position over the entire region of the M-mode image.

Preferably, the boundary detector connects the detected maximum luminance positions to perform at least one of smoothing and abnormal component removal, and then detects the maximum luminance position in a time phase corresponding to a B-mode image in which the blood vessel anterior wall boundary is detected.

It is preferable that the ultrasound diagnostic apparatus of the invention further comprises a display unit, and a region-of-interest setter which sets a region of interest in a B-mode image displayed on the display unit.

Preferably, the image producer first produces a B-mode image to be displayed on the display unit, and after a region of interest is set by the region-of-interest setter, produces a B-mode image and an M-mode image of the region of interest.

It is also preferable that a frame rate of ultrasonic waves by the ultrasound transducers is increased in response to an instruction to set the region of interest to be higher than before the instruction to set the region of interest.

The ultrasound diagnostic apparatus of the invention configured as above can appropriately and automatically detect a blood vessel anterior wall boundary, particularly, the adventitia-media boundary in the B-mode image using the M-mode image.

Therefore, according to the ultrasound diagnostic apparatus of the invention, if the position of the blood vessel anterior wall or the like in the B-mode image is necessary at the time of measurement of the blood vessel elastic modulus, it is possible to save the labor of setting the blood vessel anterior wall by the operator and perform more accurate measurement.

BRIEF DESCRIPTION OF THE DRAWINGS

FIGS. 11A to 11G are conceptual diagrams illustrating an example of image display in the ultrasound diagnostic apparatus illustrated in FIG. 1.

DETAILED DESCRIPTION OF THE INVENTION

Hereinafter, an ultrasound diagnostic apparatus of the invention will be described in detail on the basis of a preferred example illustrated in the accompanying drawings.

Figure 1:
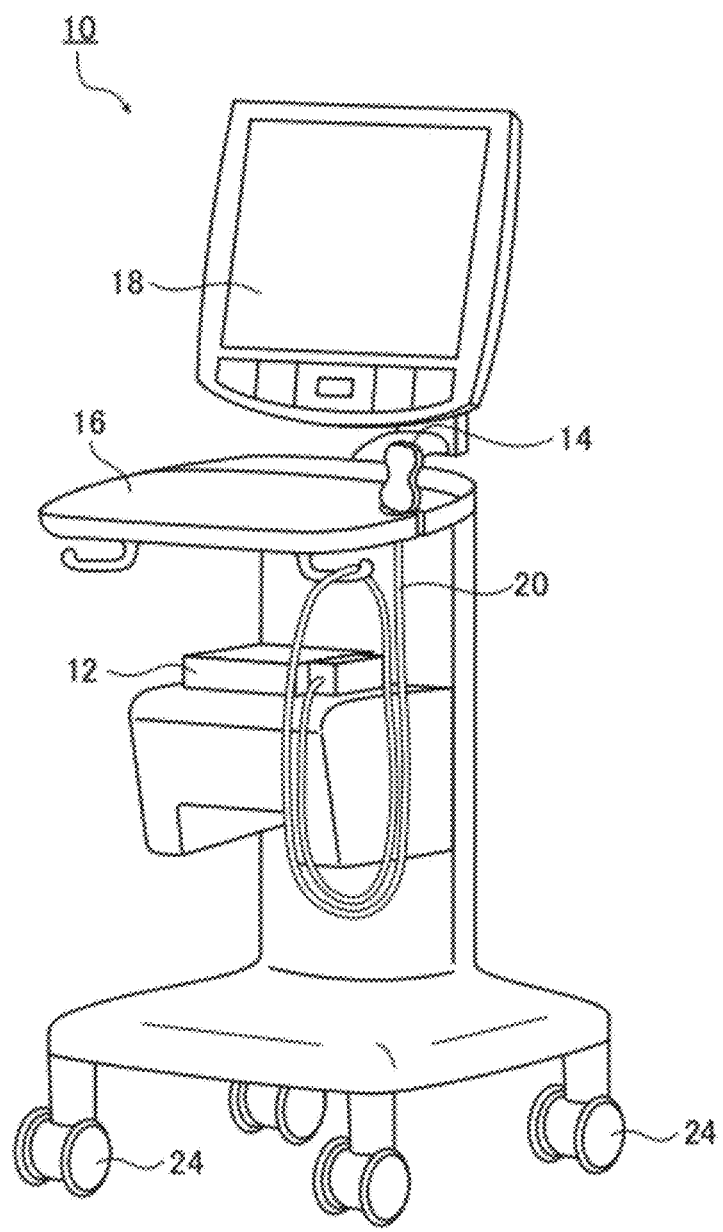
FIG. 1 is a diagram conceptually illustrating an example of an ultrasound diagnostic apparatus of the invention.

FIG. 1 conceptually illustrates the appearance of an example of the ultrasound diagnostic apparatus of the invention.

As illustrated in FIG. 1, an ultrasound diagnostic apparatus 10 basically has a diagnostic apparatus body 12, an ultrasound probe 14, an operating panel 16, and a display 18. Casters 24 are arranged at the lower end of the ultrasound diagnostic apparatus 10, such that the apparatus can be easily moved by human power.

The ultrasound probe 14 (hereinafter, referred to as a probe 14) performs transmission/reception of ultrasonic waves, and supplies a reception signal according to a received ultrasonic echo to the diagnostic apparatus body 12.

The probe 14 is a known ultrasound probe which is used in various ultrasound diagnostic apparatuses. The probe 14 has so-called ultrasound transducers (ultrasonic piezoelectric transducers) arranged in a one-dimensional or two-dimensional array which transmit ultrasonic waves toward a subject, receive an ultrasonic echo reflected by the subject, and output an electrical signal (reception signal) according to the received ultrasonic echo.

In the invention, the type of the probe 14 is not particularly limited, and various types, such as a convex type, a linear type, and a sector type, may be used. An external probe or a probe for an ultrasound endoscope, such as a radial scan type, may be used. The probe 14 may have ultrasound transducers for receiving second and higher harmonics of transmitted ultrasonic waves which correspond to harmonic imaging.

In the illustrated example, the probe 14 and the diagnostic apparatus body 12 are connected together by a cable 20.

However, the invention is not limited thereto, a transmission circuit 28, a reception circuit 30, a transmission/reception controller 32, and the like described below may be arranged in the probe 14, and the probe 14 and the diagnostic apparatus body 12 may be connected together by wireless communication.

The display 18 is a known display (display device).

In the ultrasound diagnostic apparatus 10, as in various ultrasound diagnostic apparatuses, the display 18 displays an ultrasound image according to a reception signal output from the probe 14, information of the subject, selection means or instruction means for operation by a GUI (Graphical User Interface), a region of interest (hereinafter, referred to as ROI), an elasticity measurement result of a vascular wall described below, and the like.

The operating panel 16 is provided to operate the ultrasound diagnostic apparatus 10.

Though not illustrated, in the ultrasound diagnostic apparatus 10, the operating panel 16 has arranged therein selection means for selecting various modes, such as a B mode and an M mode, a trackball (track pad/touch pad) for moving a cursor, a line, or the like displayed on the display 18, a set button for determining (confirming) selection or operation, a freeze button for switching between motion image display and still image display, changing means for changing the visual field depth of an ultrasound image, gain adjusting means, a zoom button for enlarging an ultrasound image, and the like.

As the modes of the ultrasound diagnostic apparatus 10, in addition to the modes of the normal ultrasound diagnostic apparatus, such as a B mode and an M mode, a VE mode (Vascular Elasticity Mode) for measuring the elastic modulus of the vascular wall is set.

Though not illustrated, the operating panel 16 also has arranged therein a touch panel 16a (see FIG. 6B) which is a display device for operation by GUI.

The diagnostic apparatus body 12 controls the overall operation of the ultrasound diagnostic apparatus 10, and also performs various processes for producing an ultrasound image according to the reception signal output from the probe 14, displaying the ultrasound image on the display 18, and measuring a blood vessel elastic modulus.

The diagnostic apparatus body 12 is constituted using, for example, a computer or the like.

Figure 2:
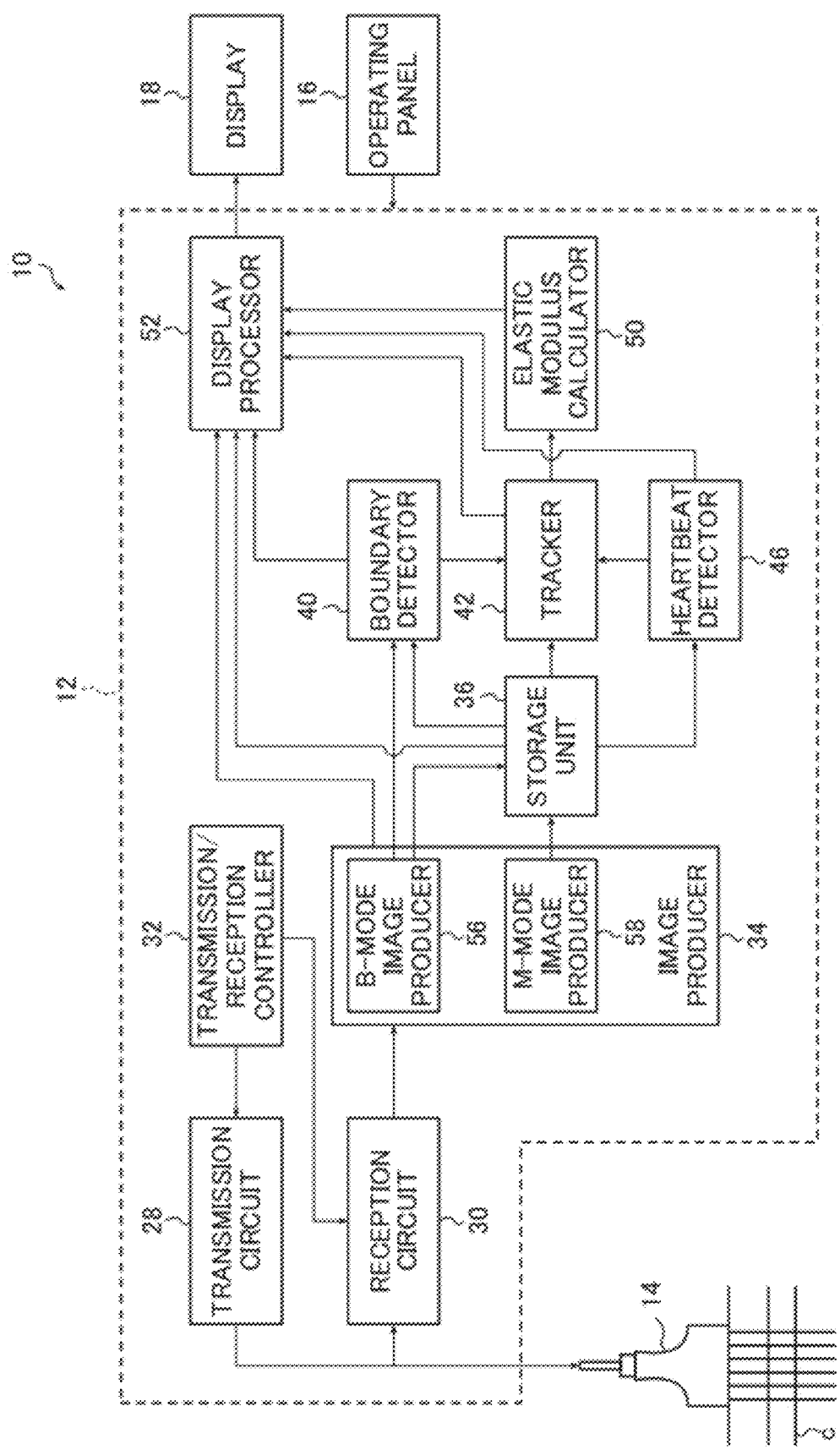
FIG. 2 is a block diagram conceptually illustrating the configuration of the ultrasound diagnostic apparatus illustrated in FIG. 1.
Figure 3:
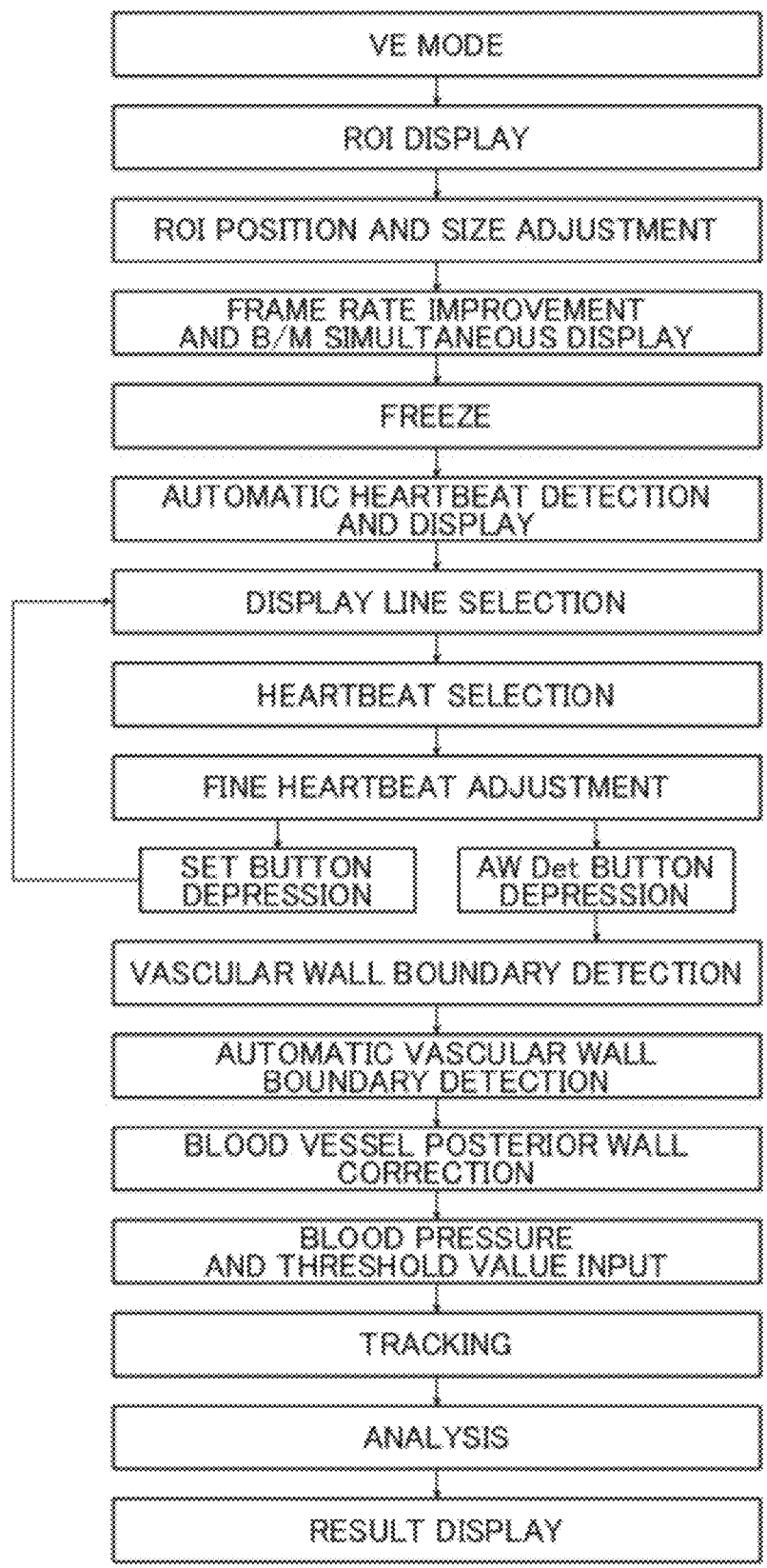
FIG. 3 is a flowchart for explaining an example of elasticity measurement of a vascular wall in the ultrasound diagnostic apparatus illustrated in FIG. 1.

FIG. 2 is a block diagram conceptually illustrating the configuration of the ultrasound diagnostic apparatus 10.

As illustrated in FIG. 2, the diagnostic apparatus body 12 has the transmission circuit 28, the reception circuit 30, the transmission/reception controller 32, an image producer 34, a storage unit 36, a boundary detector 40, a tracker 42, a heartbeat detector 46, an elastic modulus calculator 50, and a display processor 52.

The image producer 34 has a B-mode image producer 56 and an M-mode image producer 58.

The above-mentioned probe 14 is connected to the transmission circuit 28 and the reception circuit 30. The transmission/reception controller 32 is connected to the transmission circuit 28 and the reception circuit 30. The reception circuit 30 is connected to the image producer 34.

The image producer 34 is connected to the display processor 52. The B-mode image producer 56 and the M-mode image producer 58 of the image producer 34 are connected to the storage unit 36. The B-mode image producer 58 is also connected to the boundary detector 40.

The storage unit 36 is connected to the boundary detector 40, the tracker 42, the heartbeat detector 46, and the display processor 52. The boundary detector 40 and the heartbeat detector 46 are connected to the tracker 42 and the display processor 52 together. The tracker 42 is also connected to the elastic modulus calculator 50, and the elastic modulus calculator 50 is connected to the display processor 52.

The transmission/reception controller 32 sequentially sets the transmission direction of an ultrasonic beam and the reception direction of an ultrasonic echo of the probe 14 through the transmission circuit 28 and the reception circuit 30.

The transmission/reception controller 32 also has a transmission control function of selecting a transmission delay pattern in accordance with the set transmission direction and a reception control function of selecting a reception delay pattern in accordance with the set reception direction.

The transmission delay pattern is the pattern of a delay time which is given to an actuation signal of each ultrasound transducer so as to produce an ultrasonic beam to a desired direction by ultrasonic waves transmitted from a plurality of ultrasound transducers of the probe 14. The reception delay pattern is the pattern of a delay time which is given to a reception signal so as to extract an ultrasonic echo from a desired direction by ultrasonic waves received by a plurality of ultrasound transducers.

A plurality of transmission delay patterns and a plurality of reception delay patterns are stored in an internal memory (not illustrated), and are appropriately selected and used depending on the situation.

The transmission circuit 28 includes a plurality of channels, and produces a plurality of actuation signals which are respectively applied to a plurality of ultrasound transducers of the probe 14. At this time, it is possible to give the delay time to each of a plurality of actuation signals on the basis of the transmission delay pattern selected by the transmission/reception controller 32.

The transmission circuit 28 may adjust the delay amount of each of a plurality of actuation signals such that ultrasonic waves transmitted from a plurality of ultrasound transducers of the probe 14 produce an ultrasonic beam, and may respectively supply the adjusted actuation signals to the ultrasound transducers. Alternatively, the transmission circuit 28 may supply to the probe 14 a plurality of actuation signals made up such that ultrasonic waves transmitted from a plurality of ultrasound transducers at a time cover the entire imaging region of the subject.

Similarly to the transmission circuit 28, the reception circuit 30 includes a plurality of channels. The reception circuit 30 amplifies a plurality of analog signals received through a plurality of ultrasound transducers and converts the amplified analog signals to digital reception signals.

A reception focusing process is performed by giving the delay time to each of a plurality of reception signals on the basis of the reception delay pattern selected by the transmission/reception controller 32 and adding the reception signals. With this reception focusing process, the focus of the ultrasonic echo is narrowed to produce a sound ray signal (sound ray data).

The produced sound ray data is supplied to the image producer 34.

The image producer 34 performs a preprocess, such as Log (logarithmic) compression or gain adjustment, on the supplied sound ray data to produce image data of the ultrasound image, converts (raster-converts) the image data to image data based on a normal television signal scan system, performs a necessary image process, such as a gradation process, on the image data and outputs the image data to the display processor 52.

The image producer 34 has a B-mode image producer 56 which produces a B-mode image, and an M-mode image producer 58 which produces an M-mode image. The B-mode image and the M-mode image may be produced by a known method.

The display processor 52 produces display data for display on the display 18 in accordance with image data of the ultrasound image supplied from the image producer 34, image data of the ultrasound image read from the storage unit 36, operation (input instruction) on the operating panel 16, the measurement result (analysis result) of a vascular wall elastic modulus described below, and the like, and displays the display data on the display 18.

In the ultrasound diagnostic apparatus 10 of the illustrated example, the storage unit 36, the boundary detector 40, the tracker 42, the heartbeat detector 46, and the elastic modulus calculator 50 of the diagnostic apparatus body 12 are primarily used in the VE mode in which the elastic modulus of the vascular wall is measured.

Hereinafter, the respective units, such as the storage unit 36 and the boundary detector 40, and the ultrasound diagnostic apparatus 10 of the invention will be described in detail by describing the action of the ultrasound diagnostic apparatus 10 in the VE mode with reference to a flowchart of FIG. 3 and FIGS. 5 to 13.

In the following description, with regard to the display of the display 18, the display processor 52 performs necessary process, such as line production, even though not particularly described.

If an ultrasound diagnosis by the ultrasound diagnostic apparatus 10 starts, under the control of the transmission/reception controller 32, the transmission circuit 28 causes the ultrasound transducer of the probe 14 to transmit ultrasonic waves, and the reception circuit 30 processes the reception signal output from the probe 14 to produce a sound ray signal and outputs the sound ray signal to the image producer 34.

Figure 4:
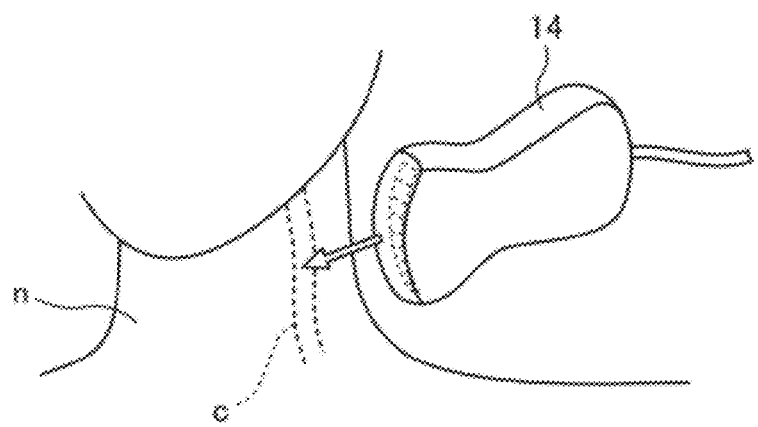
FIG. 4 is a conceptual diagram for explaining an ultrasound diagnosis for elasticity measurement of a vascular wall.

As an example, the B mode is selected, as conceptually illustrated in FIG. 4, a carotid artery c of the subject is used as a measurement target, and the probe 14 is brought into contact with a neck n. In this case, a B-mode image produced by the image producer 34 (B-mode image producer 56) is processed by the display processor 52 and displayed on the display 18.

Figure 5A:
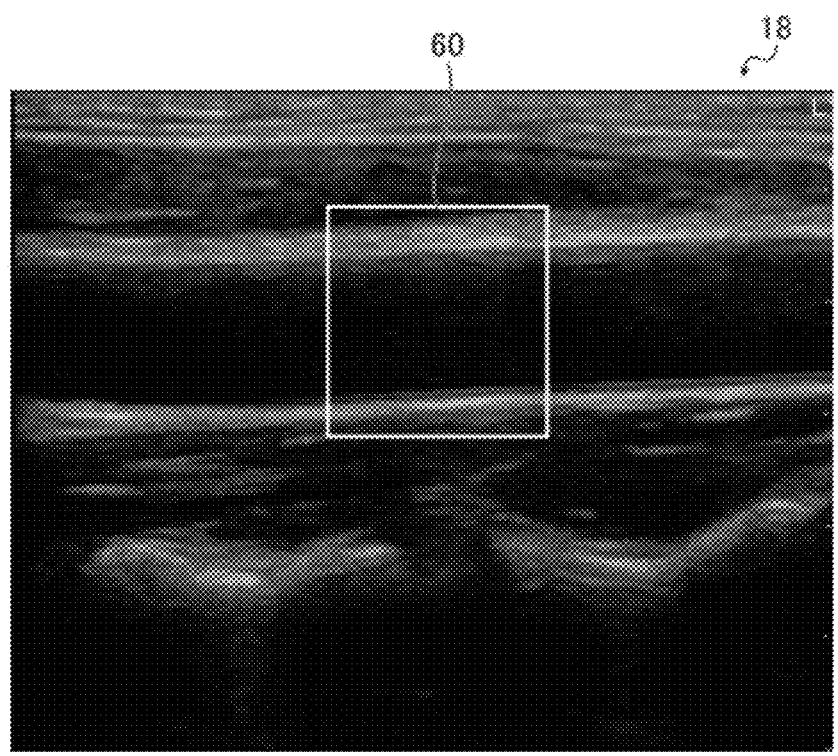
FIGS. 5A and 5B are conceptual diagrams illustrating an example of image display in the ultrasound diagnostic apparatus illustrated in FIG. 1.

If the intended carotid artery c can be observed in an appropriate state, and the VE mode is selected by mode selection means of the operating panel 16 (in the following description, "of the operating panel 16" is omitted), as conceptually illustrated in FIG. 5A, the display processor 52 displays the ROI 60 representing the region of interest in the B-mode image.

In this state, the position of the ROI 60 in the B-mode image can be moved by operation of the trackball. If the set button is depressed, the position of the ROI 60 is fixed, and the size of the ROI 60 can be changed by operation of the trackball.

Each time the set button is depressed, the position change of the ROI 60 and the size adjustment of the ROI 60 can be alternately carried out.

If the zoom button is depressed in this state, the adjustment of the position or the size of the ROI 60 ends, and an instruction to set the ROI 60 is made. In response to this situation, the transmission/reception controller 32 increases the frame rate to be higher than before the instruction to set the ROI 60 (for example, to be equal to or higher than 200 Hz, or at least five times higher than before the ROI setting instruction). In addition, the M-mode image producer 58 starts to produce an M-mode image of the ROI 60, and as illustrated in FIG. 5B, a B-mode image 64 where the portion of the ROI 60 is enlarged and an M-mode image 65 of the ROI 60 (at the position of a selection line 62) are displayed simultaneously.

The simultaneous display (dual mode display) of the B-mode image 64 and the M-mode image 65 may be performed in the same manner as so-called B/M-mode display in the known ultrasound diagnostic apparatus.

Figure 5B:
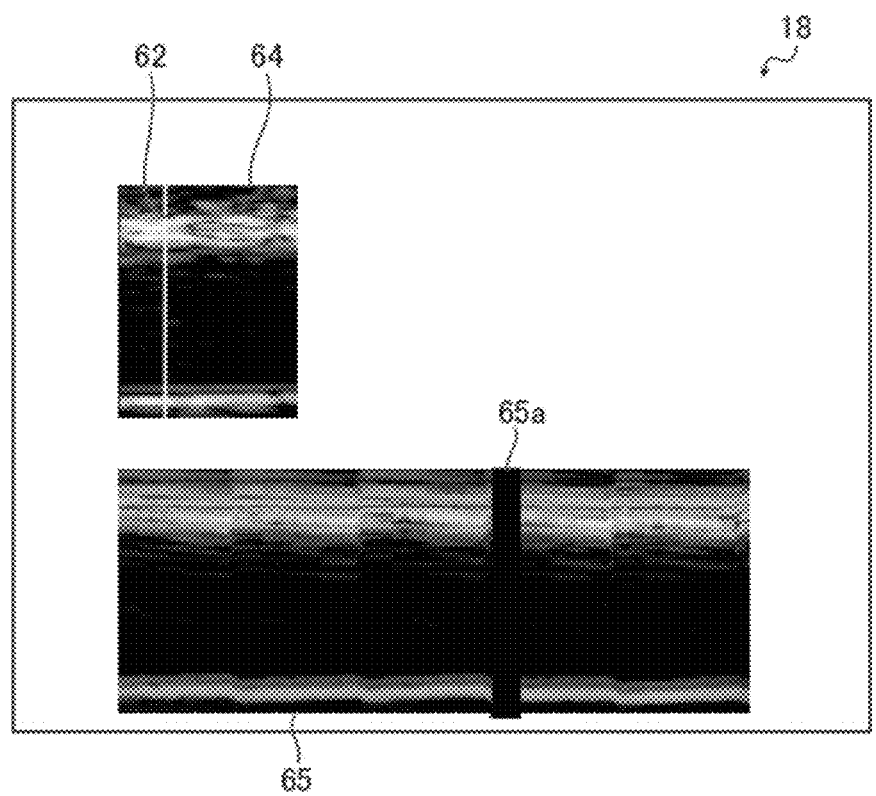

In FIG. 5B, the upper side is the B-mode image 64, and the lower side is the M-mode image 65.

In the B-mode image 64, the horizontal direction of the drawing is the azimuth direction (the arrangement direction of the ultrasound transducers (in the two-dimensional arrangement, the longitudinal direction)), and the vertical direction is the depth direction (the transmission/reception direction of ultrasonic waves). The upper side in the depth direction is the side on which the depth is shallow (the probe 14 side).

A selection line 62 which extends in the depth direction to select the display position of the M-mode image (the display line of the M-mode image) in the azimuth direction in the B-mode image is displayed in the B-mode image. The selection line 62 is movable in the azimuth direction (left-right direction) by the trackball.

In the M-mode image 65, the horizontal direction is the direction of the time axis. In the M-mode image 65, the time flows from left to right, and the left side of a gap 65a becomes a current frame (that is, the right side of the gap 65a is a previous frame). Similarly to the B-mode image 64, the vertical direction is the depth direction. The upper side in the depth direction is the side on which the depth is shallow.

In FIG. 5B, the M-mode image 65 displayed on the display 18 is the M-mode image 65 at the position of the selection line 62 set in advance.

The M-mode image producer 58 produces an M-mode image at a predetermined position (a predetermined position set in advance or a selected position) in the azimuth direction or a selected position in the azimuth direction as well as over the entire region of the B-mode image 64 in the azimuth direction.

The B-mode image (B-mode image data) of the ROI 60 produced by the B-mode image producer 56 and the M-mode image (M-mode image data) produced by the M-mode image producer 58 are stored in the storage unit 36 together.

The temporal amount of an image which is stored in the storage unit 36 is not particularly limited, while a duration including two or more common heartbeats is preferred. Accordingly, it is preferable that the storage unit 36 stores the latest B-mode image and M-mode image which are each three seconds or longer in duration.

As described above, the selection line 62 can be moved in the azimuth direction by the trackball.

The position of the selection line 62 and the M-mode image are moved together. That is, if the selection line 62 is moved in the left-right direction by the trackball, the display processor 52 displays the M-mode image of the position of the selection line 62 on the display 18.

The operator depresses the freeze button if it is determined that an appropriate image is obtained.

Figure 6A:
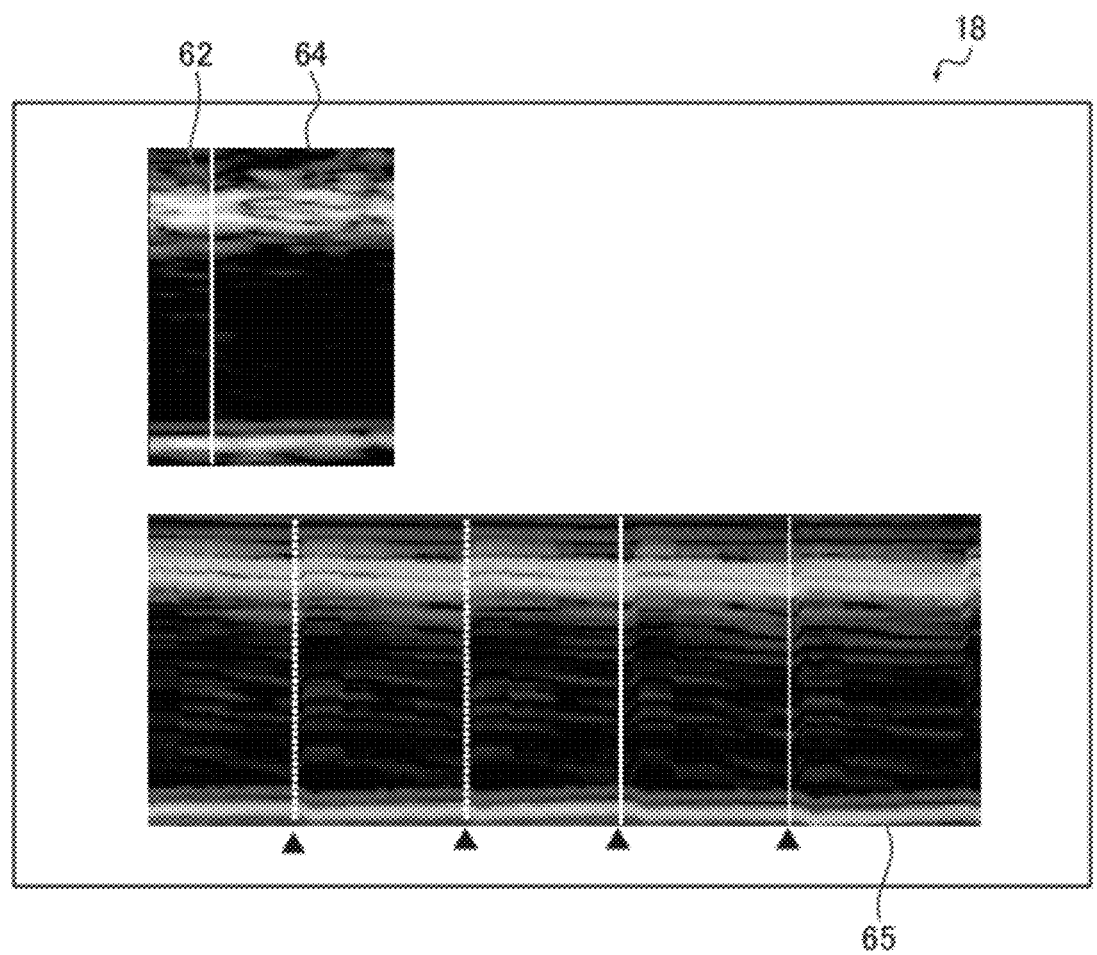
FIGS. 6A and 6B are conceptual diagrams illustrating an example of image display in the ultrasound diagnostic apparatus illustrated in FIG. 1.

If the freeze button is depressed, the display processor 52 reads necessary image data from the storage unit 36, and as illustrated in FIG. 6A, the display processor 52 rearranges the M-mode image 65 of the position of the selection line 62 such that the time at which the freeze button is depressed is on the rightmost side (latest position) and displays the still image of the M-mode image 65 with the still image of the B-mode image 64 on the display 18. Simultaneously, the selection line 62 becomes a broken line and is not movable (inactive state).

Figure 6B:
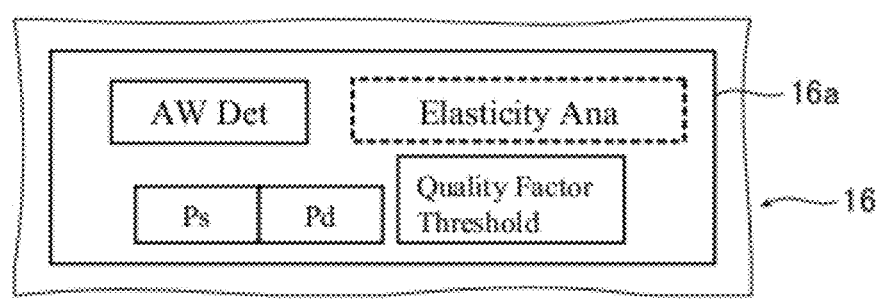

As illustrated in FIG. 6B, an "AW Det" button for instructing to set the boundary of the vascular wall described below, an "Elasticity Ana" button for instructing to start the analysis of the vascular wall elastic modulus, a "Ps" button and a "Pd" button for inputting the blood pressure of the subject, and a "Quality Factor Threshold" button for inputting a reliability threshold value are displayed on the touch panel 16a of the operating panel 16. At this time, the "Elasticity Ana" button is not selectable.

If the freeze button is depressed, the heartbeat detector 46 detects the heartbeats (automatically detects the heartbeats) for all the M-mode images stored in the storage unit 36. The detection result of the heartbeats is sent to the storage unit 36, and added to the corresponding M-mode image as information.

The detection result of the heartbeats is also sent to the display processor 52, and the detection result of the heartbeats is displayed in the M-mode image 65 which is currently displayed.

The method of detecting the heartbeats is not particularly limited. As an example, an M-mode image may be analyzed, and the heartbeats may be detected using the moving velocity (the time at which the velocity starts to increase) in the depth direction of a white line (bright line) extending in the horizontal direction, the pulsation of the motion in the depth direction of the white line, or the like. Alternatively, an electrocardiograph (electrocardiogram) may be used to detect the heartbeats.

As illustrated in FIG. 6A, the display processor 52 displays the detection result of the heartbeats in the M-mode image 65 by a triangular mark and a line. In the illustrated example, the time at which the latest heartbeat starts is indicated by a solid line, the time at which the same heartbeat ends is indicated by a thin line, and the position related to other heartbeats is indicated by a broken line. The lines may be distinguished by changing the line color instead of or in addition to the line type.

When there is the heartbeat which is not detected, the heartbeat is displayed at an appropriate position in accordance with the interval of heartbeats prior to and subsequent to the heartbeat in question, or the like.

The B-mode image 64 when the freeze button is depressed is a B-mode image at the time when the latest heartbeat starts, with the time being indicated in the M-mode image 65 by a solid line.

If the lines of the heartbeats are displayed in the M-mode image 65, the selection line 62 in the B-mode image becomes a solid line and is movable in the left-right direction by the trackball. That is, the selection line 62 is in the active state. Whether or not the line is active may be distinguished by changing the line color instead of or in addition to the line type in a similar manner to the above.

In this state, if the selection line 62 is moved in the left-right direction by the trackball, the display processor 52 reads an M-mode image corresponding to the position of the selection line 62 from the storage unit 36, and displays the image on the display 18 along with the detection result of the heartbeats. That is, the selection line 62 is moved by the trackball even after freeze, thereby selecting the display position (display line) of the M-mode image 65 in the B-mode image 64 over the entire region in the azimuth direction in the B-mode image 64.

Therefore, according to this example, the M-mode image 65 of an arbitrary position in the azimuth direction of the set ROI 60 is displayed, such that the M-mode image 65 and an image corresponding to each heartbeat in the M-mode image can be observed and confirmed.

Figure 7A:
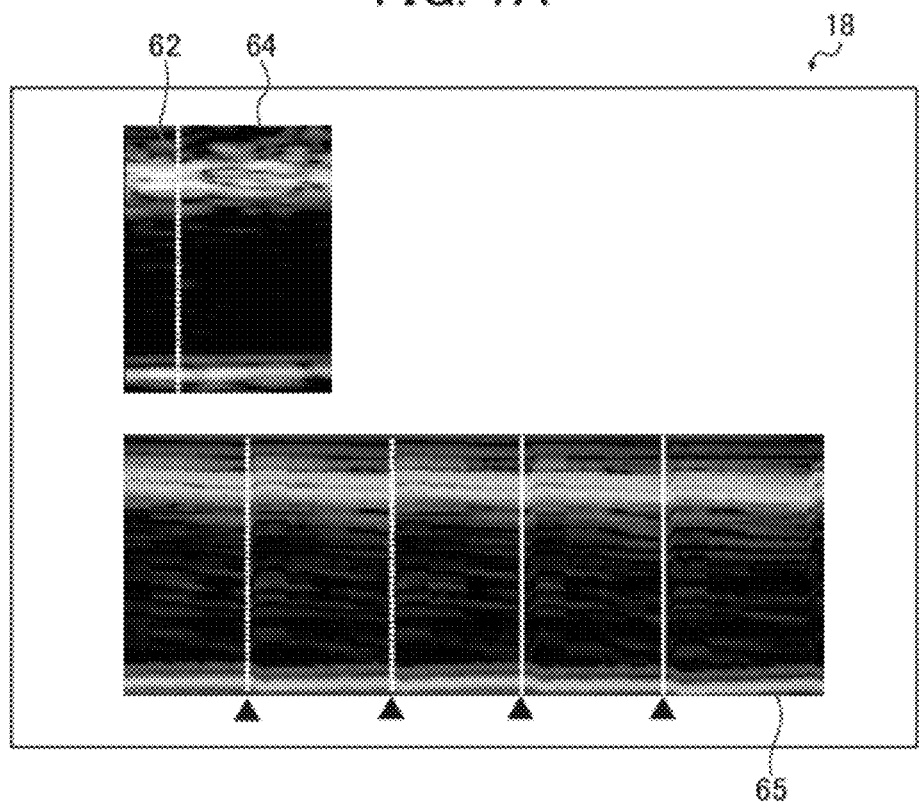
FIGS. 7A to 7C are conceptual diagrams illustrating an example of image display in the ultrasound diagnostic apparatus illustrated in FIG. 1.

If the set button is depressed in a state where the selection line 62 of the B-mode image 64 is movable, it is determined that the display position (display line) of the M-mode image is selected. As illustrated in FIG. 7A, the selection line 62 of the B-mode image 64 becomes a broken line, such that the movement by the trackball is impossible. Simultaneously, lines indicating the latest heartbeat become a solid line in the M-mode image 65.

If the lines indicating the latest heartbeat become a solid line in the M-mode image 65, the heartbeat is selectable by the trackball.

Figure 7B:
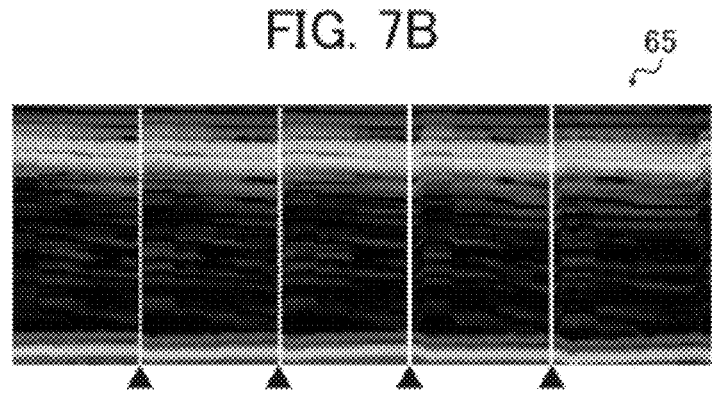
Figure 7C:
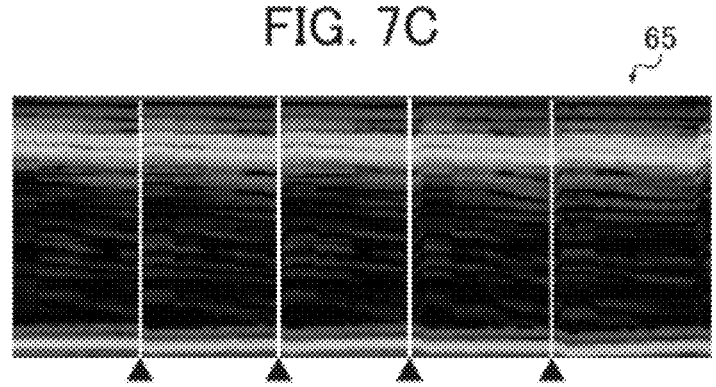

As an example, when the set button is depressed, as illustrated in FIGS. 7A and 7B, the lines indicating the latest heartbeat become a solid line, and the heartbeat is selected. In this state, for example, if the trackball rotates left, as illustrated in FIG. 7C, a line corresponding to the end of the latest heartbeat becomes a broken line, lines corresponding to the second latest heartbeat become a solid line, and the heartbeat is selected. If the trackball further rotates left, lines corresponding to the second latest heartbeat become a broken line, lines corresponding to the third latest heartbeat become a solid line, and the heartbeat is selected.

If the trackball rotates right, similarly, lines corresponding to later heartbeats are sequentially selected.

In response to the selection of the heartbeat in the M-mode image 65, the display processor 52 reads from the storage unit 36, the B-mode image at the start position of the selected heartbeat, that is, the B-mode image which is captured at the time (time phase) corresponding to the start position of the selected heartbeat, and changes the B-mode image 64 displayed on the display 18 to this image.

If the set button is depressed in a state where the heartbeats are selectable, it is determined that the selection of the heartbeats ends, the selected heartbeat is confirmed, and fine adjustment of the selected heartbeat can be performed.

If a heartbeat in the M-mode image 65 displayed on the display 18 is selected and confirmed, the same heartbeat is selected in all the M-mode images (that is, the M-mode images over the entire region in the azimuth direction of the B-mode image 64) stored in the storage unit 36.

Figure 8A:
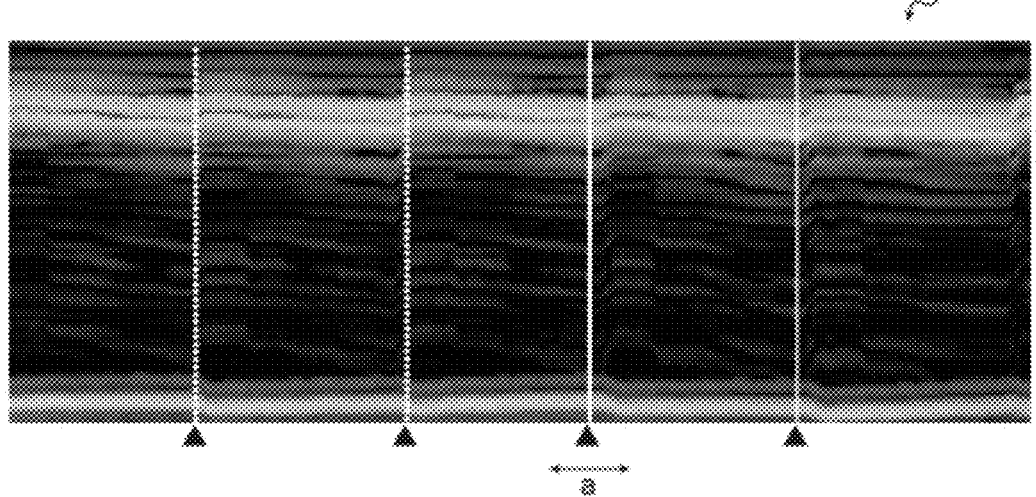
FIGS. 8A and 8B are conceptual diagrams illustrating an example of image display in the ultrasound diagnostic apparatus illustrated in FIG. 1.

As an example, if it is determined that the latest heartbeat is selected and the set button is depressed, as illustrated in FIG. 8A, first, a line corresponding to the end of the selected heartbeat becomes a thin line, and the position (time) of a line corresponding to the start of the selected heartbeat is movable in the left-right direction (time direction) by the trackball as indicated by an arrow a, such that fine adjustment of the start position of the heartbeat can be performed.

Figure 8B:
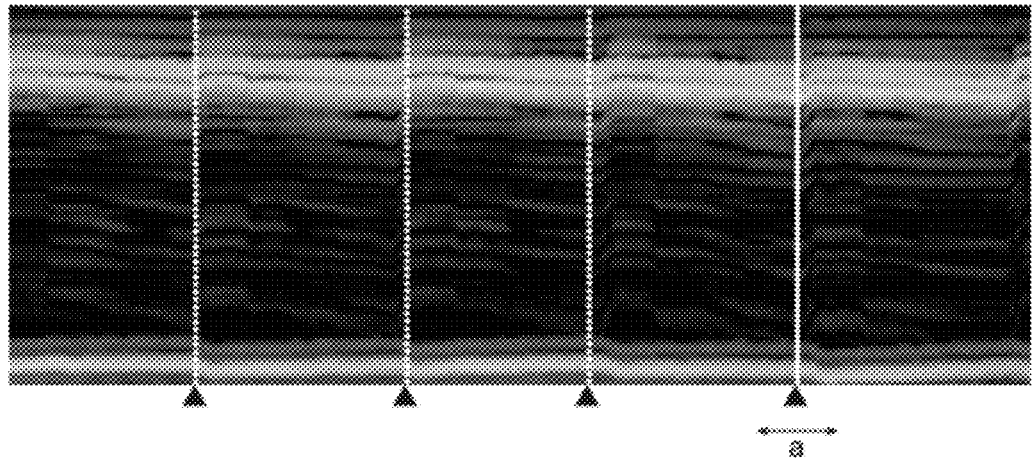

If the set button is depressed after the start position of the heartbeat is adjusted by the trackball as required, as illustrated in FIG. 8B, a line corresponding to the end of the selected heartbeat becomes a normal solid line, and a line corresponding to the start of the selected heartbeat becomes a thin line. Accordingly, the position of the line corresponding to the end of the selected heartbeat is movable in the left-right direction by the trackball as indicated by the arrow a, such that fine adjustment of the end position of the heartbeat can be performed.

Although the result of fine adjustment of the heartbeat may be reflected only in the M-mode image 65 subjected to fine adjustment, it is preferable that the result is also reflected in all the M-mode images stored in the storage unit 36.

When the start position of the heartbeat is adjusted in the selected heartbeat, the display processor 52 reads the B-mode image at the adjusted heartbeat start position from the storage unit 36, and the B-mode image 64 displayed on the display 18 is changed to this image.

The results of heartbeat selection and possible fine adjustment are also supplied to the tracker 42.

If the set button is depressed in a state where the position corresponding to the end of the selected heartbeat is adjustable, the state where the selection line 62 of the B-mode image 64 illustrated in FIG. 6A is movable, that is, the state where the display line of the M-mode image 65 is selectable in the B-mode image 64 is returned.

That is, in the ultrasound diagnostic apparatus 10 of the illustrated example, the processes "display line selection"→"heartbeat selection"→"heartbeat fine adjustment" can be repeatedly performed. In other words, the processes "display line selection"→"heartbeat selection"→"heartbeat fine adjustment" may be performed in a looped manner.

Accordingly, it becomes possible to more suitably select the heartbeat most appropriate for analysis to measure the vascular wall elasticity described below from all the stored M-mode images.

Figure 9:
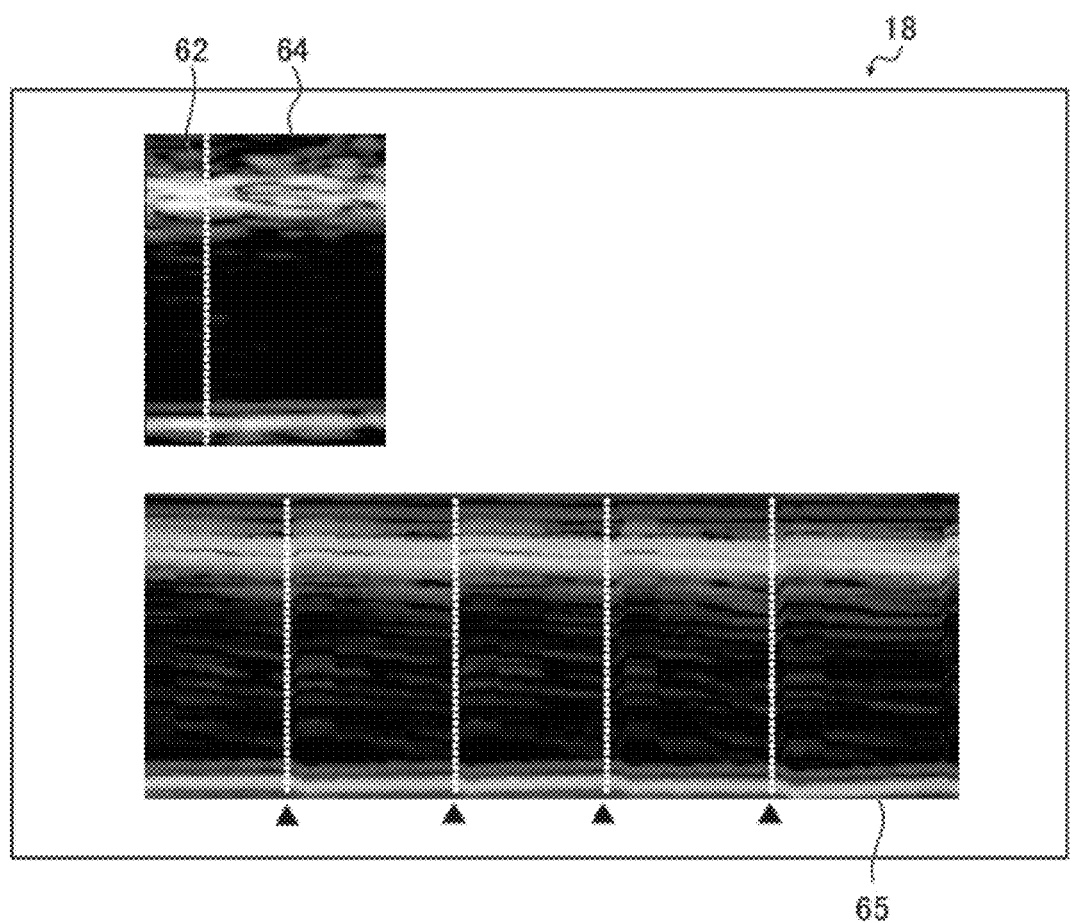
FIG. 9 is a conceptual diagram illustrating an example of image display in the ultrasound diagnostic apparatus illustrated in FIG. 1.

If the "AW Det" button of the touch panel, not the set button, is depressed in a state where the position corresponding to the end of the selected heartbeat is adjustable, as illustrated in FIG. 9, the selection line 62 of the B-mode image 64 and the lines representing the heartbeats in the M-mode image 65 all become a broken line and are inoperable, and a vascular wall detection mode is reached.

In the vascular wall detection mode, the adventitia-media boundary of the blood vessel anterior wall, the intima-lumen boundary of the blood vessel anterior wall, the intima-lumen boundary of the blood vessel posterior wall, and the adventitia-media boundary of the blood vessel posterior wall are detected by the boundary detector 40.

The boundary detector 40 initially sets a temporary lumen of the blood vessel so as to detect the adventitia-media boundary of the blood vessel anterior wall.

In the blood vessel, basically, there is no tissue which reflects ultrasonic waves in the lumen. Accordingly, in the M-mode image, the lumen is seen as a low-luminance band extending in the time axis direction. Using such event, the boundary detector 40 first binarizes the M-mode image 65 on the basis of luminance (density) to detect a band-like low-luminance region, and sets this region as a temporary lumen.

Figure 10A:
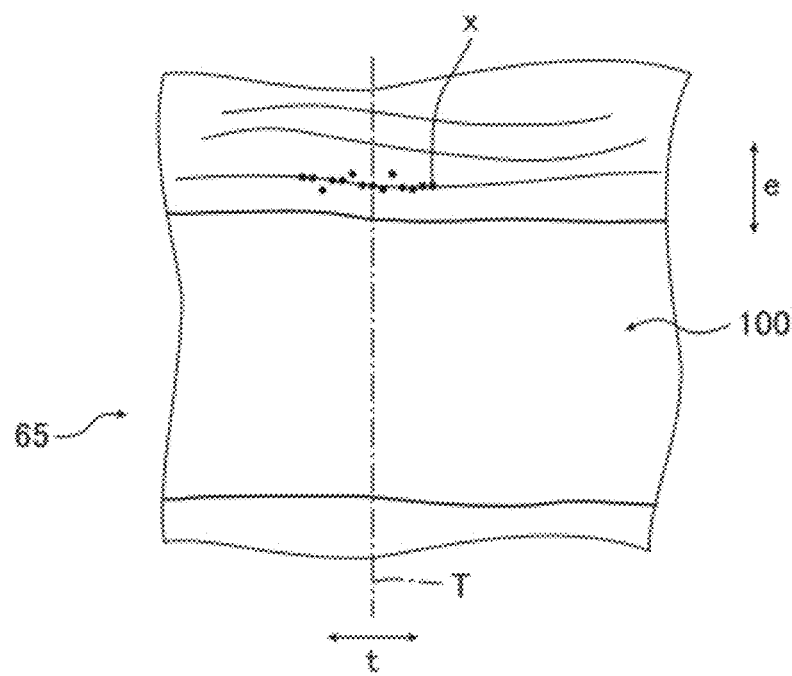
FIGS. 10A and 10B are conceptual diagrams illustrating a method of detecting an adventitia-media boundary of a blood vessel anterior wall in the ultrasound diagnostic apparatus of the invention.

Next, as conceptually illustrated in FIG. 10A, the boundary detector 40 detects a maximum luminance point (minimum density point) x in a region within 3 mm in the depth direction (arrow e direction) from the boundary of a lumen 100 temporarily set in the M-mode image 65.

In general, the gap between the adventitia-media boundary and the intima-lumen boundary of the anterior wall is normally equal to or smaller than 1 mm, and there is almost no case where the gap exceeds 3 mm. In the ultrasound image, there are many cases where the anterior wall in the B-mode image is very unclear, and there are many cases where the adventitia-media boundary of the anterior wall in the M-mode image can be detected as a high-luminance point (line).

Accordingly, in the M-mode image 65, the maximum luminance point x is detected in the region within 3 mm in the depth direction from the temporary lumen 100, thereby detecting the adventitia-media boundary in each time phase of the selection line 62 in the B-mode image 64.

As illustrated in FIG. 10A, the boundary detector 40 detects the maximum luminance point x for all frames (all temporal sampling points) in a predetermined region t (predetermined period) of the M-mode image 65 centering on a time phase T of the B-mode image 64. In the illustrated example, since the B-mode image 64 at the starting point of the selected heartbeat is displayed, the maximum luminance point x is detected for all frames in the predetermined region t centering on the starting point of the heartbeat.

The predetermined region t is not particularly limited, but may be appropriately set in accordance with required precision. In general, it should suffice that the predetermined region has a length corresponding to about one beat. Specifically, a period of about one heartbeat (about one second), of about 20 frames, of about 1/10 of the frame rate, or a period of about 0.2 $t_0$ before and after the time phase T when the length of the selected heartbeat is $t_0$ (about 0.2 seconds) may be used. Alternatively, the operator may select the predetermined region t from the options of these examples or the like, the operator may arbitrarily set the predetermined region t, or the optional selection of the predetermined region t and the arbitrary setting thereof may be made selectable.

Figure 10B:
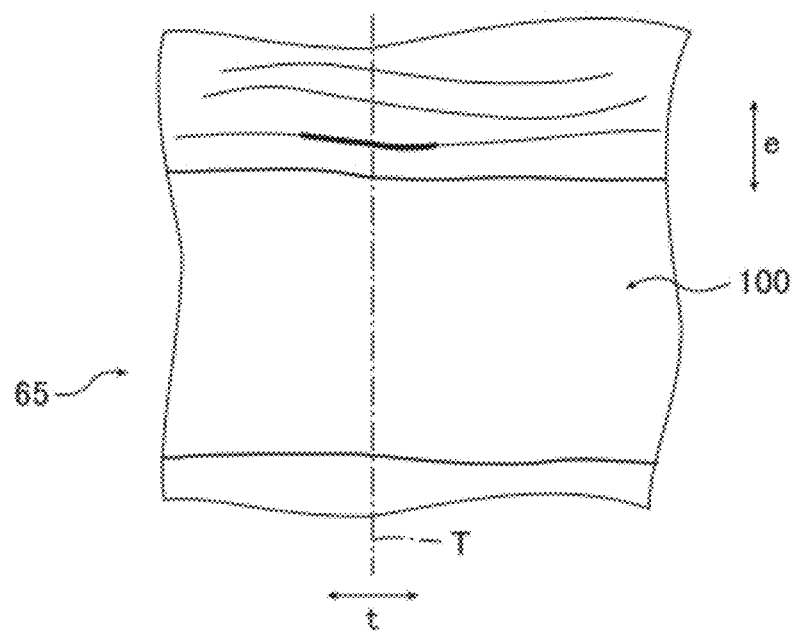

Next, as conceptually illustrated in FIG. 10B, the detected maximum luminance points x are connected, and at least one of smoothing and removal of abnormal samples is performed. The obtained line is regarded as the detection result of the adventitia-media boundary of the anterior wall in the M-mode image 65.

The detected maximum luminance points x may include an abnormal component or noise due to speckle or the like. Accordingly, the above-described process is performed to remove an abnormal component or noise due to speckle or the like, making it possible to more accurately detect the adventitia-media boundary of the anterior wall.

Smoothing or removal of abnormal components may be performed by a known method which is conducted in various image processors or the like.

In order to detect the adventitia-media boundary of the anterior wall with higher precision, the detection of the adventitia-media boundary in the M-mode image 65, that is, the detection of the maximum luminance point x may be performed over the entire region of the M-mode image in the time axis direction, not in the predetermined region t only, and the process, such as smoothing, may be performed.

To the contrary, the detection of the maximum luminance point x may be performed at only one point of the time phase T corresponding to the B-mode image 64 of the M-mode image.

Otherwise, in the detection region of the maximum luminance point x, the detection of the maximum luminance point x may be performed for every other frame, every third frame, or the like, and the process, such as smoothing, may be performed.

Alternatively, the operator may select any one of these.

After the process, such as smoothing, ends, the boundary detector 40 detects the position in the depth direction of the intersection of the adventitia-media boundary (the line thereof) detected in the M-mode image 65 and the time phase T corresponding to the B-mode image 64. That is, the intersection is the position of the adventitia-media boundary on the selection line 62 for displaying the M-mode image 65 in the B-mode image 64 being displayed.

As described above, the storage unit 36 stores M-mode images corresponding to the entire region of the B-mode image 64 in the azimuth direction, as well as the M-mode image corresponding to the selection line 62.

The boundary detector 40 similarly performs the detection of the maximum luminance point x, the detection of the adventitia-media boundary by smoothing or the like, and the detection of the intersection of the detected adventitia-media boundary and the time phase T corresponding to the B-mode image 64 in all the M-mode images stored in the storage unit 36.

That is, the detected intersections show the adventitia-media boundary at the positions in the azimuth direction, to which respective M-mode images correspond, in the B-mode image 64 being displayed.

After the intersection, that is, the adventitia-media boundary is detected in all the M-mode images, the boundary detector 40 connects the adventitia-media boundaries detected in the respective M-mode images in accordance with the positions of the respective M-mode images in the azimuth direction while fitting the positions of the adventitia-media boundaries in the depth direction to the B-mode image 64 being displayed, and sends the result to the display processor 52 as the detection result of the adventitia-media boundary of the anterior wall in the B-mode image 64.

As illustrate in FIG. 11A, the display processor 52 displays the supplied detection result of the adventitia-media boundary of the anterior wall in the B-mode image 64 as a line 68.

As described above, there are many cases where the blood vessel anterior wall is unclear in the B-mode image, and it is very difficult to automatically detect the anterior wall boundary from the B-mode image. When the positional information of the anterior wall in the B-mode image is necessary, it is necessary for the operator to set the blood vessel anterior wall manually while viewing the unclear B-mode image, causing a heavy burden to be imposed on the operator.

In contrast, in the invention, it is possible to detect the blood vessel anterior wall boundary (adventitia-media boundary) in the B-mode image using the M-mode image corresponding to the B-mode image.

For this reason, according to the invention, it is possible to avoid the labor of setting the blood vessel anterior wall or the like by the operator or to significantly reduce the burden, and also it is possible to perform more accurate measurement.

Although in this example, the adventitia-media boundary of the anterior wall in the B-mode image 64 is detected using all the M-mode images in the azimuth direction, the invention is not limited thereto.

For example, the adventitia-media boundary of the anterior wall in the B-mode image 64 may be detected in a similar manner using M-mode images extracted at a predetermined interval in the azimuth direction, such as every other image or every fourth image, instead of all the M-mode images in the azimuth direction.

Alternatively, the detection of the adventitia-media boundary of the anterior wall may be performed in a similar manner using one M-mode image or a plurality of M-mode images corresponding to a point or a plurality of points in the azimuth direction of the B-mode image, the detection result may be displayed in the B-mode image 64 in accordance with the position of the used M-mode image or images in the azimuth direction, and with this display, the operator may set the adventitia-media boundary of the anterior wall using the trackball or the like in a similar manner to the setting of a posterior wall boundary described below.

Alternatively, the operator may select one of these.

After the detection of the adventitia-media boundary of the anterior wall ends, next, the boundary detector 40 detects the intima-lumen boundary of the anterior wall.

In the M-mode image, basically, the adventitia-media boundary and the intima-lumen boundary ought to make the same motion. Meanwhile, in the M-mode image, noise due to speckle or the like makes a motion unrelated to the motion of the adventitia-media boundary, or the position thereof in the depth direction is fixed.

Using this, the boundary detector 40 detects a boundary moving in a similar manner to the adventitia-media boundary in each M-mode image using information of the temporary lumen 100 previously detected and information of the adventitia-media boundary detected in the relevant M-mode image, and regards the boundary thus detected as the intima-lumen boundary in the relevant M-mode image.

Similar to the above, the detection may be performed only in a predetermined region centering on the time phase T of the B-mode image or over the entire region along the time axis of the M-mode image.

Thereafter, similarly to the detection of the adventitia-media boundary, the intersection of the line of the intima-lumen boundary detected in each M-mode image and the time phase T of the B-mode image is detected. The intersections are arranged in accordance with the positions of the M-mode images in the azimuth direction, and then sent to the display processor 52 as the detection result of the intima-lumen boundary of the anterior wall in the B-mode image 64.

As illustrated in FIG. 11B, the display processor 52 displays the supplied detection result of the intima-lumen boundary of the anterior wall in the B-mode image 64 as a line 70.

If the detection result of the intima-lumen boundary of the anterior wall is displayed, next, as illustrated in FIG. 11C, a straight line 72 which corresponds to the intima-lumen boundary of the blood vessel posterior wall and extends in the azimuth direction is displayed in the B-mode image 64.

The line 72 is parallel-movable in the up-down direction (depth direction) by the trackball. After the line 72 is displayed, as illustrated in FIGS. 11C and 11D, the line 72 is moved to the position of the intima-lumen boundary of the blood vessel posterior wall by the trackball, and then, the set button is depressed.

As will become apparent from FIGS. 11A to 11G or other drawings, in the B-mode image, the blood vessel posterior wall boundary is displayed very clearly. Accordingly, when setting the blood vessel posterior wall by the trackball or the like, very little burden is imposed on the operator.

If the set button is depressed, as illustrated in FIG. 11E, the line 72 corresponding to the intima-lumen boundary of the blood vessel posterior wall becomes a broken line and is confirmed in the B-mode image 64, and a line 74 corresponding to the adventitia-media boundary of the blood vessel posterior wall is displayed.

Similarly, the line 74 is also movable in the up-down direction by the trackball. After the line 74 is moved to the position of the adventitia-media boundary of the blood vessel posterior wall, the set button is depressed.

The information of each boundary of the vascular wall is supplied to the boundary detector 40.

If the set button is depressed in a state where the line 74 is movable, the setting of the lines corresponding to all the boundaries ends, and the boundary detector 40 automatically detects the intima-lumen boundary and the adventitia-media boundary of the posterior wall using the set line 72 of the intima-lumen boundary and the set line 74 of the adventitia-media boundary. The result of the automatic detection of both boundaries is sent to the display processor 52 and the tracker 42, and as illustrated in FIG. 11F, the detection result is displayed.

The method of automatically detecting these boundaries is not particularly limited, and various methods may be used. As an example, a method is used in which a B-mode image is analyzed, continuous high-luminance portions at the positions of the line 72 and the line 74 are tracked to detect the intima-lumen boundary and the adventitia-media boundary.

If the automatic detection of the intima-lumen boundary and the adventitia-media boundary of the blood vessel posterior wall by the boundary detector 40 ends, as illustrated in FIG. 11F, a cursor 78 is displayed in the B-mode image 64 (the cursor 78 is not displayed until the automatic detection of the blood vessel posterior wall ends).

The cursor 78 is movable by the trackball. If the cursor 78 is moved to the line representing the automatically detected intima-lumen boundary or adventitia-media boundary, and the set button is depressed, the line closer to the cursor 78 becomes a solid line. The line which has become a solid line is correctable.

For example, as illustrated in FIG. 11G, it is assumed that the line 74 representing the adventitia-media boundary is selected and becomes a solid line. If the cursor 78 is moved along the line 74 by the trackball, and the set button is depressed again, the line 74 of the region tracked by the cursor is detected again by the boundary detector 40 and rewritten, and the result is sent to the tracker 42.

Figure 12A:
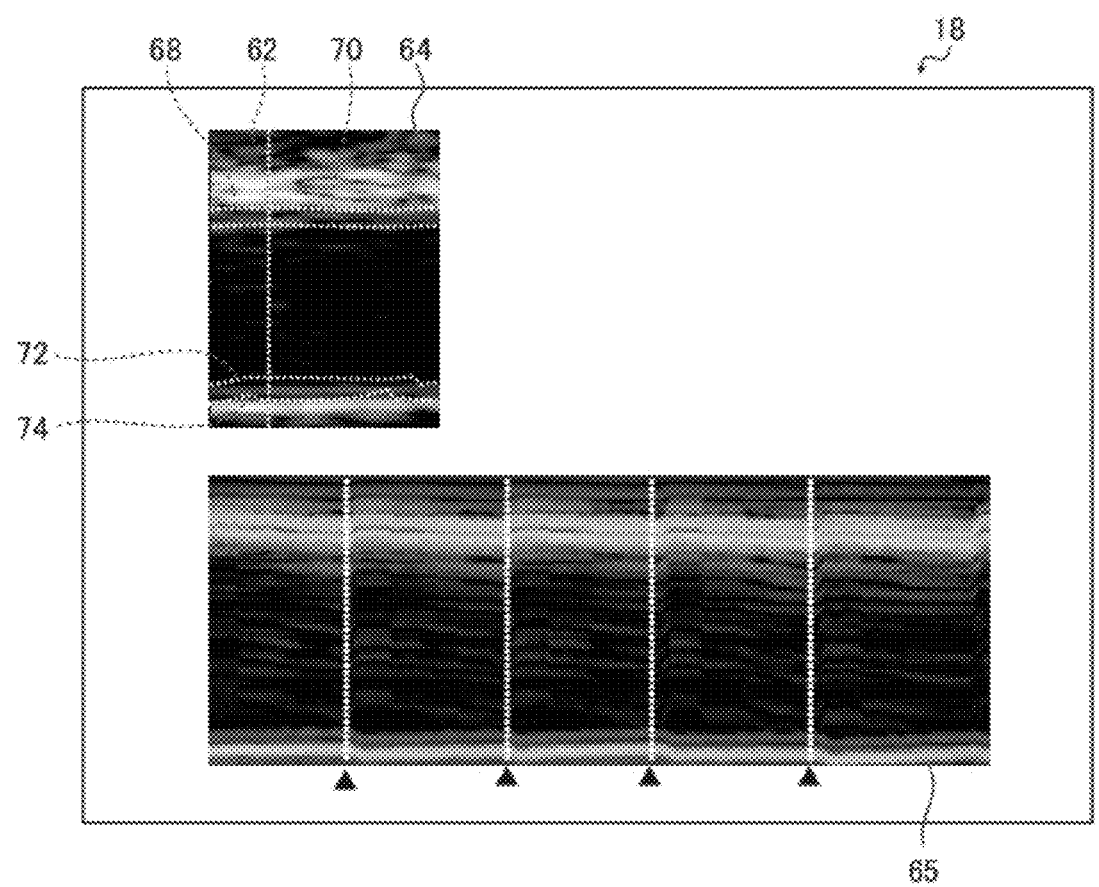
FIGS. 12A and 12B are conceptual diagrams illustrating an example of image display in the ultrasound diagnostic apparatus illustrated in FIG. 1.
Figure 12B:
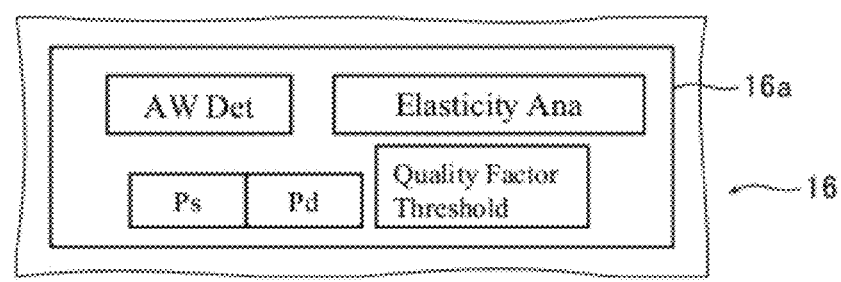

If the automatic detection of the intima-lumen boundary and the adventitia-media boundary of the posterior wall ends, and if necessary, the blood vessel posterior wall is corrected, as illustrated in FIG. 12A, all lines become a broken line, and as illustrated in FIG. 12B, the "Elasticity Ana" button of the touch panel 16a is selectable.

After the "Elasticity Ana" button is selectable, the blood pressure in the heart systole of the subject is input by the "Ps" button, the blood pressure in the heart end diastole of the subject is input using the "Pd" button, and the reliability threshold value is input using the "Quality Factor Threshold" button. These numerical values may be input by a known method.

The input of the blood pressure of the subject and the reliability threshold value is not limited to the input after the detection of the vascular wall boundaries has ended. The input may be performed at any timing before analysis described below starts (before the "Elasticity Ana" button described below is depressed).

In the ultrasound diagnostic apparatus 10, it is usual that before a diagnosis is performed, the subject information is acquired or input. Accordingly, when the subject information includes the information of the blood pressure, the information of the blood pressure may be used.

If the blood pressure of the subject and the reliability threshold value are input, and the "Elasticity Ana" button is depressed, analysis of the B-mode image starts, and the elastic modulus of the vascular wall is calculated.

If the "Elasticity Ana" button is depressed, first, the tracker 42 tracks the motions of the blood vessel anterior wall (adventitia-media boundary and intima-lumen boundary) and the blood vessel posterior wall (intima-lumen boundary and adventitia-media boundary) in the selected heartbeat in the M-mode image 65. That is, the blood vessel anterior wall and posterior wall are tracked.

The tracking of the vascular wall in the M-mode image 65 is performed with the adventitia-media boundary of the blood vessel anterior wall, the intima-lumen boundary of the blood vessel anterior wall, the intima-lumen boundary of the blood vessel posterior wall, and the adventitia-media boundary of the blood vessel posterior wall previously detected (set) in the B-mode image 64 as a positional starting point (a starting point in the depth direction).

In regard to the tracking of the vascular wall in the M-mode image 65, a temporal starting point (a starting point on the time axis of the M-mode image) is the time phase of the B-mode image 64, that is, the time at which the B-mode image 64 is captured. That is, in the illustrated example, the start position of the heartbeat which is selected and, if necessary, adjusted in position becomes the temporal starting point for the tracking of the vascular wall.

In the ultrasound diagnostic apparatus 10, as a preferred form, not only the detected (set) boundaries of the vascular wall but also one or more measurement points in the depth direction may be set in the blood vessel posterior wall. In this way, when one or more measurement points are set in the blood vessel posterior wall, the tracking of the vascular wall is performed at each measurement point.

The measurement point in the vascular wall may be set in advance, may be automatically set on the basis of a specific algorithm, or may be set by the operator of the ultrasound diagnostic apparatus 10 while viewing the image. These may be used in combination.

The method of tracking the vascular wall in the M-mode image 65 is not particularly limited, and there are a method which uses continuity of images (luminance) from the starting point of the tracking, a pattern matching method, a zero crossing method, a tissue Doppler method, phase difference tracking, and the like. Of these, any method may be used.

With regard to the blood vessel anterior wall, when the detection of the maximum luminance point in the M-mode image is performed over the entire region of the heartbeat, the detection result of the adventitia-media boundary or the like by the detection of the maximum luminance point may be used as the tracking result of the blood vessel anterior wall. Alternatively, the tracking of the blood vessel anterior wall may be performed using (with reference to) the detection result (obtained for a portion or the whole of the heartbeat) of the adventitia-media boundary or the like based on the M-mode image.

The tracking result of the vascular wall in the M-mode image by the tracker 42 is supplied to the elastic modulus calculator 50 and the display processor 52.

The elastic modulus calculator 50 first produces the change waveform of the thickness of the vascular wall (intima-media) and the change waveform of the blood vessel diameter (inner diameter) from the tracking result of the vascular wall. As described above, when one or more measurement points are set in the vascular wall, the change waveform of the vascular wall is produced between the measurement points.

The change waveform of the thickness of the vascular wall and the change waveform of the blood vessel diameter are sent to the display processor 52.

The elastic modulus calculator 50 calculates strain in the radial direction of the blood vessel using Equation (1).

$$\epsilon_i = \Delta h_i / h_{di} \qquad (1)$$

In Equation (1), $\epsilon_i$ denotes strain in the radial direction of the blood vessel between the measurement points, $\Delta h_i$ denotes the maximum value of a change in thickness of the vascular wall between the measurement points in the heart systole in which the vascular wall is smallest in thickness in one heartbeat, and $h_{di}$ denotes the thickness between the measurement points in the heart end diastole in which the vascular wall is largest in thickness.

The elastic modulus calculator 50 calculates an elastic modulus $E_{\theta i}$ in the circumferential direction of the vascular wall by Equation (2) using the maximum value and the minimum value of the blood pressured input in advance.

$$E_{\theta i} = \tfrac{1}{2} * [1 + (r_d/h_d)] * [\Delta p/(\Delta h_i/h_{di})] \qquad (2)$$

An elastic modulus $E_{ri}$ in the radial direction of the vascular wall may be calculated by Equation (3).

$$E_{ri} = \Delta p/(\Delta h_i/h_{di}) \qquad (3)$$

In Equations (2) and (3), $\Delta h_i$ and $h_{di}$ are the same as described above, $\Delta p$ denotes a blood pressure difference between the heart systole and the heart end diastole, $r_d$ denotes the radius of the vascular lumen in the heart end diastole, and $h_d$ denotes the thickness of the vascular wall in the heart end diastole.

After the elastic modulus is calculated, the elastic modulus calculator 50 calculates reliability of the elastic modulus.

The method of calculating reliability of the elastic modulus is not particularly limited, and various known methods may be used. As an example, there is a method in which the waveforms of changes in the blood vessel diameter by the heartbeats of many people, such as 1000 persons are prepared, the model waveform of the change in the blood vessel diameter is created from many waveforms, and reliability of the calculated elastic modulus is calculated using the amount of a shift from the model waveform.

As described above, if a heartbeat is selected and confirmed in the M-mode image displayed on the display 18, the same heartbeat is selected in all the M-mode images stored in the storage unit 36.

Accordingly, the processes, such as the tracking of the vascular wall, the production of the change waveforms of the thickness of the vascular wall and the blood vessel diameter, the calculation of strain of the vascular wall, and the calculation of the elastic modulus of the vascular wall and reliability of the elastic modulus, are performed in the selected heartbeat for not only the M-mode image 65 displayed on the display 18 but also all the M-mode images stored in the storage unit 36. That is, the processes, such as calculation of the elastic modulus of the vascular wall, in the selected heartbeat are performed over the entire region in the azimuth direction of the B-mode image 64 displayed on the display 18 using the corresponding M-mode images.

These results are added to the M-mode images stored in the storage unit 36 as information.

After the calculation over the entire region in the azimuth direction ends, the elastic modulus calculator 50 calculates the average value ($E_{\theta ave}$) of the elastic modulus of the vascular wall, the average value ($Str_{ave}$) of strain of the vascular wall, and the average value ($QF_{ave}$) of reliability of the elastic modulus.

If the calculation ends, the result is displayed on the display 18.

Figure 13:
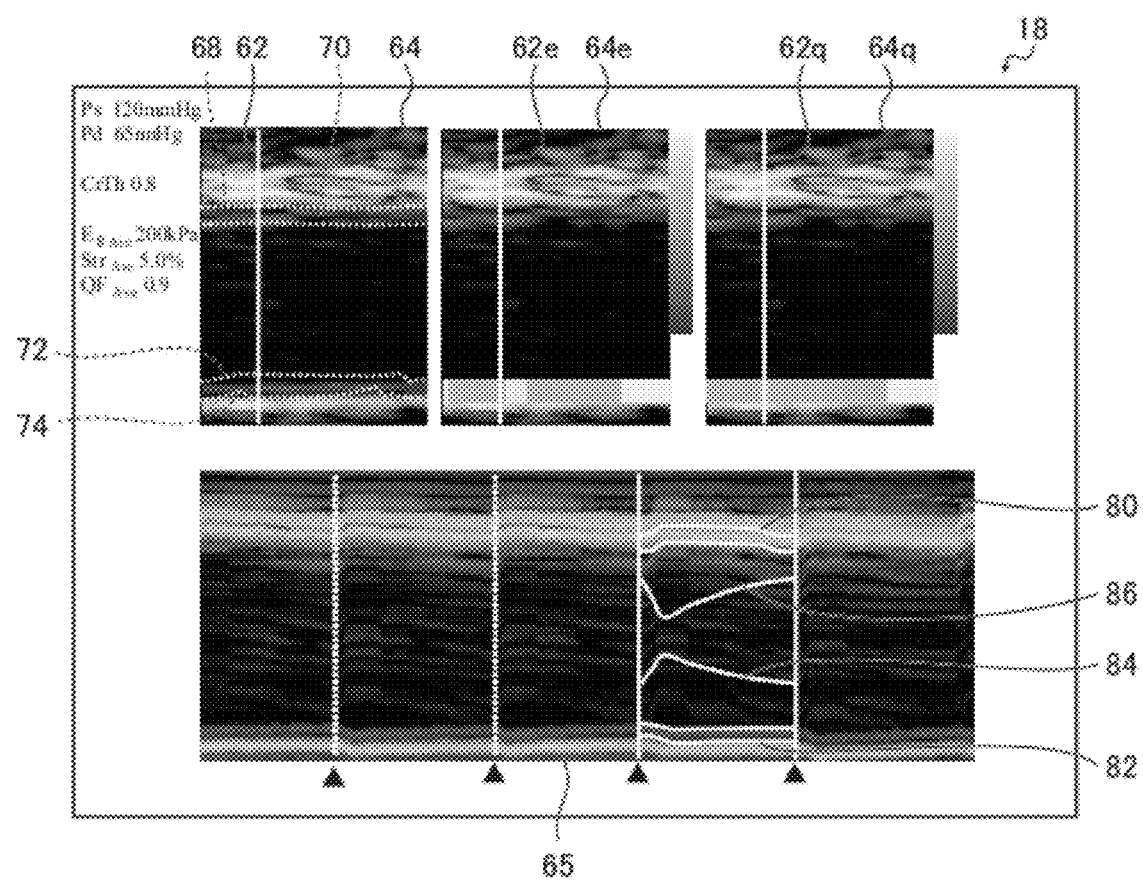
FIG. 13 is a conceptual diagram illustrating an example of image display in the ultrasound diagnostic apparatus illustrated in FIG. 1.

FIG. 13 illustrates an example. In the illustrated example, on the right side of the displayed B-mode image 64, the elastic modulus of the blood vessel posterior wall represented in the B-mode image 64 is displayed by a B-mode image 64*e*. On the right side of the B-mode image 64*e* which displays the elastic modulus of the blood vessel posterior wall, reliability of the elastic modulus of the vascular wall is displayed by a B-mode image 64*q* in a similar manner.

On the left side of the B-mode image 64, the average value ($E_{\theta ave}$) of the elastic modulus of the vascular wall, the average value ($Str_{ave}$) of strain of the vascular wall, and the average value ($QF_{ave}$) of reliability of the elastic modulus are respectively displayed.

The elastic modulus of the vascular wall is displayed in a strip shape in the B-mode image 64*e* to overlap the blood vessel posterior wall automatically detected (and corrected as necessary) in the B-mode image 64. On an upper right side of the B-mode image 64*e*, the index of the elastic modulus is displayed. In the illustrated example, the higher the image density, the higher the elastic modulus.

That is, in the B-mode image 64*e*, the density of the strip overlapping the blood vessel posterior wall represents the elastic modulus of the vascular wall at the corresponding position of the blood vessel.

Similarly, reliability of the elastic modulus is displayed in a strip shape in the B-mode image 64*q* to overlap the blood vessel posterior wall automatically detected in the B-mode image 64. On an upper right side of the B-mode image 64*q*, the index of reliability of the elastic modulus is displayed. In the illustrated example, the higher the image density, the higher reliability of the elastic modulus.

That is, in the B-mode image 64*q*, the density of the strip overlapping the blood vessel posterior wall represents reliability of the vascular wall elastic modulus at the corresponding position of the blood vessel.

The magnitude of the elastic modulus or reliability of the elastic modulus may be realized by changing the image color instead of or in addition to the image density.

In the display of the result illustrated in FIG. 13, the result is automatically omitted at the position in the azimuth direction where reliability of the result is lower than a threshold value input in advance.

With regard to the position where the result is omitted, as represented in a right corner portion of the result display of the elastic modulus in the B-mode image 64*e* or a right corner portion of the result display of reliability in the B-mode image 64*q*, the display of the strip is thinned.

In the lower M-mode image 65, a tracking result 80 of the blood vessel anterior wall, a tracking result 82 of the blood vessel posterior wall, a change waveform 84 of the blood vessel diameter, and a change waveform 86 of the thickness of the vascular wall in the M-mode image are displayed in the selected heartbeat.

As described above, when one or more measurement points are set in the vascular wall in the depth direction, the change waveform of the blood vessel thickness may be output between the measurement points.

If the measurement result of the elastic modulus of the vascular wall or the like is displayed on the display 18, the selection line 62 becomes a solid line in the B-mode image 64, and is movable in the azimuth direction by the trackball.

If the selection line 62 is moved in the B-mode image 64, the display processor 52 reads the M-mode image corresponding to the position of the selection line 62 from the storage unit 36 and displays the M-mode image on the display 18. That is, if the selection line 62 is moved by the trackball, the M-mode image 65 is changed to the M-mode image at the position of the selection line 62, and the tracking results 80 and 82 of the blood vessel anterior wall and the blood vessel posterior wall, the change waveform 84 of the blood vessel diameter and the change waveform 86 of the thickness of the vascular wall in the M-mode image are changed to data at the position of the selection line 62 of the B-mode image 64.

Accordingly, it is possible to select the display line for displaying the M-mode image 65 and the analysis result over the entire region in the azimuth direction of the B-mode image.

After the set button is depressed, in the B-mode image 64e and the B-mode image 64q, if a selection line 62e and a selection line 62q are moved by the trackball to select an arbitrary region in the azimuth direction, and thereafter, the set button is depressed again, the selected region is handled in a similar manner to the above-mentioned region where reliability is lower than the threshold value, and data is deleted.

That is, the tester views the result, and when there is a location where the waveform or the like seems to be extraordinary, data can be deleted, thereby making it possible to perform more accurate analysis.

The state after the deletion of data may be returned in a previous state by depressing a Delete button or the like.

Although the ultrasound diagnostic apparatus of the invention has been described in detail, the invention is not limited to the foregoing examples, and various modifications or improvements may be of course made without departing from the scope of the invention.

The ultrasound diagnostic apparatus of the invention can be suitably used in medical practice for the diagnosis of arteriosclerosis which causes myocardial infarction, angina pectoris, brain diseases, or the like.

What is claimed is:

1. An ultrasound diagnostic apparatus comprising:
an ultrasound probe which has ultrasound transducers transmitting ultrasonic waves, receiving an ultrasonic echo reflected by a subject, and outputting a reception signal according to the received ultrasonic echo;
an image producer which produces a B-mode image and an M-mode image from the reception signal output from the ultrasound transducers; and
a boundary detector which detects an adventitia-media boundary of a blood vessel anterior wall in the B-mode image using a time phase corresponding to the B-mode image of the M-mode image,
wherein the image producer produces M-mode images corresponding to a plurality of points in an azimuth direction of the B-mode image, and
wherein the boundary detector, in each of the M-mode images corresponding to a plurality of points in the azimuth direction of the B-mode image, binarizes the M-mode image based on luminance to detect a band-like low-luminance region, sets the band-like low-luminance region as a temporary lumen, detects a maximum luminance position within 3 mm in a depth direction from the temporary lumen for all frames in a predetermined region of the M-mode image with having, as a center, a time phase of the M-mode image corresponding to the B-mode image in which the adventitia-media boundary of the blood vessel anterior wall is detected, connects the detected maximum luminance positions to perform at least one of smoothing and abnormal component removal and regards an obtained line as a detection result of an adventitia-media boundary of a blood vessel anterior wall in the M-mode image, detects a position in the depth direction of intersection of the adventitia-media boundary of the blood vessel anterior wall detected in the M-mode image and the time phase corresponding to the B-mode image, and sets the detected position in the depth direction of the intersection as an adventitia-media boundary of a blood vessel anterior wall in the B-mode image, and, in the B-mode image, locates and connects adventitia-media boundaries detected in all of the M-mode images in accordance with positions of the respective M-mode images in the azimuth direction while fitting positions of the adventitia-media boundaries in the depth direction to the B-mode image, thereby detecting the adventitia-media boundary of the anterior wall in the B-mode image.

2. The ultrasound diagnostic apparatus according to claim 1, wherein the image producer produces M-mode images corresponding to an entire region in the azimuth direction of the B-mode image.

3. The ultrasound diagnostic apparatus according to claim 1, wherein the boundary detector detects the maximum luminance position over an entire region of the M-mode image.

4. The ultrasound diagnostic apparatus according to claim 1, further comprising:
a display unit; and
a region-of-interest setter which sets a region of interest in a B-mode image displayed on the display unit.

5. The ultrasound diagnostic apparatus according to claim 4, wherein the image producer first produces the B-mode image to be displayed on the display unit, and after the region of interest is set by the region-of-interest setter, produces a B-mode image and an M-mode image of the region of interest.

6. The ultrasound diagnostic apparatus according to claim 4, wherein a frame rate of ultrasonic waves by the ultrasound transducers is increased in response to an instruction to set the region of interest to be higher than before the instruction to set the region of interest.

* * * * *